(12) United States Patent
Nishii et al.

(10) Patent No.: US 7,211,409 B2
(45) Date of Patent: May 1, 2007

(54) STANDARD COMPOUND FOR IMMUNOASSAY FOR DIOXIN AND METHOD OF IMMUNOASSAY FOR DIOXIN

(75) Inventors: Shigeaki Nishii, Tsuruga (JP); Kazuhiro Matsui, Tsuruga (JP); Takuya Ishibashi, Tsuruga (JP); Masanori Oka, Tsuruga (JP); Hiroki Fujihira, Takasago (JP); Hirotsugu Mishima, Takasago (JP); Shizuo Kataoka, Takasago (JP)

(73) Assignees: Toyo Boseki Kabushiki Kaisha, Osaka (JP); Takuma Co., Ltd., Osaka (JP)

( * ) Notice: Subject to any disclaimer, the term of this patent is extended or adjusted under 35 U.S.C. 154(b) by 0 days.

(21) Appl. No.: 10/525,626

(22) PCT Filed: Aug. 18, 2003

(86) PCT No.: PCT/JP03/10394

§ 371 (c)(1),
(2), (4) Date: Feb. 24, 2005

(87) PCT Pub. No.: WO2004/020397

PCT Pub. Date: Mar. 11, 2004

(65) Prior Publication Data

US 2006/0166296 A1    Jul. 27, 2006

(30) Foreign Application Priority Data

Aug. 29, 2002 (JP) .............................. 2002-251616

(51) Int. Cl.
G01N 33/545 (2006.01)
G01N 33/535 (2006.01)
C07K 17/02 (2006.01)

(52) U.S. Cl. .................. 435/7.93; 435/7.92; 435/7.95; 530/405; 530/406

(58) Field of Classification Search ................. 562/472; 435/7.92, 7.93, 7.95; 530/405, 406, 388.9, 530/389
See application file for complete search history.

(56) References Cited

U.S. PATENT DOCUMENTS

| | | | | |
|---|---|---|---|---|
| 5,538,852 A | * | 7/1996 | Carlson et al. ............... | 435/7.9 |
| 5,834,222 A | * | 11/1998 | Friedman et al. ........... | 435/7.93 |
| 2003/0054424 A1 | * | 3/2003 | Allen et al. ................. | 435/7.92 |
| 2004/0191846 A1 | * | 9/2004 | Fujihira et al. ............. | 435/7.92 |

FOREIGN PATENT DOCUMENTS

| EP | 0 455 058 A | 11/1991 |
|---|---|---|
| JP | 2002-128731 | 5/2002 |
| JP | 2002-131316 | 5/2002 |
| JP | 2002-155023 | 5/2002 |
| JP | 2002-277467 | 9/2002 |

OTHER PUBLICATIONS

Hatzidakis et al. Use of L-lysine fluorescence derivatives as tracers to enhance the performance of polarization fluoroimmunoassays. A study using two herbicides as model antigens. Anal. Chem. 2002, vol. 74, pp. 2513-2521.*

Feung et al. Metabolism of 2,4-dichlorophenoxyacetic acid. IV. mass spectra and chromatographic properties of amino acid conjugates. J. Agr. Food Chem. 1973, vol. 21, No. 4, pp. 632-637.*

Dioxin, PAN Pesticides database: http://www.pesticideinfo.org/Detail_Chemical.jsp?Rec_Id=PC35857.*

Synopsis on dioxins and PCBs: http://www.ktl.fi/dioxin/atoc.html.*

Arjmand, M. et al., (1976) Metabolism of 2, 4-dichlorophenoxyacetic acid. 8. Gas liquid chromatography of trimethylsilyl derivatives of amino acid conjugates., J. of Agricultural and Food Chem. 24(3):574-580.

Kelley, M. et al., (1987) "The effect of pretreatment with 2, 3, 7, 8-tetrachlorodibenzo-p-dioxin on the hepatic metabolism of 2, 4, 5-trichlorophenoxy acetate (2, 4, 5-T) and 2, 4- dichlorophenoxy acetate (2, 4-D)", Toxicology and Applied Pharmacology 91(2):295-298.

Mitchum, R.K. et al. (1980) "Application of Negative Ion Atmospheric Pressure Ionization (NIAPI) mass spectrometry for trace analysis", Advances in Mass Spectrometry, No. 8B pp. 1415-1421.

Chiu et al. (1995) "A Monoclonal Immunoassay for the Coplanar Polychlorinated Biphenyls," Analytical Chemistry, 67(21):3829-3839.

Fujihira et al. (2003) "Development of a Quick and Efficient Analysis Method of Dioxins Using Elisa," Organohalogen Compounds 60:311-314.

(Continued)

*Primary Examiner*—Long V. Le
*Assistant Examiner*—Shafiqul Haq
(74) *Attorney, Agent, or Firm*—Fish & Richardson P.C.

(57) ABSTRACT

A compound of formula (1) and an immunoassay method for quantitative determination of dioxins in a sample using as a standard the compound of the following formula (1):

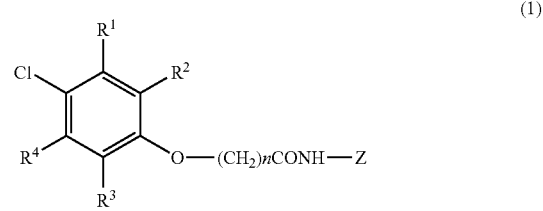

(1)

wherein $R^1$, $R^2$, $R^3$ and $R^4$ may be the same or different and represent chlorine or hydrogen, n is an integer from 1 to 10, and Z represents an amino acid residue or peptide.

28 Claims, 5 Drawing Sheets

OTHER PUBLICATIONS

Fujihira et al. (2003) "Development of the Rapid & Efficient Analysis Method for the Dioxins Using Enzyme-Linked Immuno-Sorbent Assay (ELISA)," Journal of Resources and Environment 39(6):62-64.

Fujihira et al. (2003) "Highly-sensitive rapid determination of the dioxins—Measurement principle and characteristics—," Environment Cleaning Technology 2(5):63-66.

* cited by examiner

Correlation with instrumental analysis measurement of exhaust gas samples (n=29)

Fig. 4

Correlation with instrumental analysis measurement of fly ash samples (n=13)

Fig. 5

Correlation with instrumental analysis measurement of soil samples (n=9)

STANDARD COMPOUND FOR IMMUNOASSAY FOR DIOXIN AND METHOD OF IMMUNOASSAY FOR DIOXIN

RELATED APPLICATIONS

This is a U.S. national phase filing under 35 U.S.C. § 371 of PCT/JP03/10394 filed Aug. 18, 2003 and claims priority from JP 2002-251616 filed Aug. 29, 2002.

TECHNICAL FIELD

The present invention relates to an immunoassay standard for dioxins. The present invention further relates to an immunoassay method for dioxins using this standard, and more specifically to a method of computing the concentration or toxic equivalent (TEQ) of dioxins in the air, exhaust gases, soils, rivers, combustion ashes and the like using a dioxin analogue as a reference.

BACKGROUND ART

Dioxins is a general term for polychlorinated dibenzo-p-dioxins (PCDDs), polychlorinated dibenzofurans (PCDFs), and coplanar polychlorinated biphenyls (Co-PCBs). A great number of isomers that differ in the chlorine substitution patterns exist for these three types of skeletal structures. Among the isomers of PCDDs and PCDFs, those having chlorine substituents at the 2-, 3-, 7-, and 8-positions are highly toxic and known to cause dermatitis, multiple neurosis, nystagmus, hepatic insufficiency and like symptoms due to the chlorine substitution.

It is also known that long-term exposure to dioxins even in low concentrations can cause chronic symptoms such as porphyria cutanea tarda and also exhibit various toxic properties such as teratogenicity and carcinogenicity.

Furthermore, in recent years, so-called "endocrine disruptors" having the action of disrupting endocrine functions in humans and wild animals have been the focus of attention as a global environmental problem. It has also been revealed that dioxins might be an endocrine disruptor having estrogen activity.

It has become clear that dioxins with their various toxic properties are contained in chemicals such as herbicides and insecticides, exhaust gases and fly ashes from garbage incineration facilities, waste water from papermills, etc. Dioxins are thus detected not only in environmental samples from the air, soils, waters and sediments of rivers, harbors and ports around big cities, etc. but also in biological samples such as foods, blood, urine and mothers' milk. Since such a widespread contamination of the environment has been a big social problem, there is a pressing need to know the amount of dioxin exposure in the environment.

The measurement of dioxins requires high-precision analytical data. Therefore, official methods that comprise extracting, concentrating and purifying dioxins using various chromatographic techniques and subsequent analysis using an expensive analyzer such as a high resolution gas chromatography/mass spectrometer are conventionally used. Such analytical methods are highly sensitive and capable of multi-component analysis so that two or more compounds can be identified and quantitatively determined at one time. On the other hand, such methods have problems in that capital investment such as expensive special equipment and clean rooms is necessary and specialists who are skilled in analysis are required and it takes a long time to obtain results because of the complicated pretreatment.

For such reasons, the development of a highly sensitive, easy dioxin immunoassay method is desired. Environmental pollutant detection techniques using an antibody immunoassay have attracted attention to achieve this object.

Immunoassay is a method for detecting or quantitatively determining a trace amount of an antigen using the capacity of an antibody to specifically recognize the antigen, whereby the antigen can be measured with high sensitivity due to the high affinity and high specificity of the antibody for the antigen. Thus immunoassay has various merits such as simplicity in pretreatment of samples, easy and quick measurement of multiple samples and low cost per measurement, and has been used in a wide variety of fields such as medicine, biochemistry, pharmaceutical sciences and agriculture. To detect or quantitatively determine the targeted substance by immunoassay, it is necessary to label the antibody or antigen, and various labeling methods have been developed. Due to its simplicity, enzyme immunoassay (EIA) using an enzyme has widely been used in clinical tests and the biochemistry field to quantitatively determine targeted substances in biological samples. EIA can be roughly classified into competitive assays and non-competitive assays, based on the form of antigen-antibody interaction. Low molecular weight compounds such as dioxins are usually determined by competitive assays.

In EIA, the concentration of a targeted compound in a sample is calculated from a standard curve that is prepared by using the same compound as the targeted compound as a standard and quantitatively determining the standard in the same manner as the sample. However, since dioxins encompass isomers of three types of compounds having different skeletal structures, the isomers being different in the chlorine substitution pattern, it is difficult to decide which compound should be used as a standard.

Since the toxicity of dioxins differs among congeners and isomers, the toxicity level of dioxins, a mixture of congeners and isomers having different toxicities, varies depending on the ratio of the constituent isomers. A simple sum of the individual isomer amounts does not accurately represent dioxin toxicity.

Many of the dioxin EIA systems so far developed utilize the most toxic 2,3,7,8-tetrachlorobenzo-p-dioxin (2,3,7,8-TeCDD) as a standard (Anal. Chem. 70, 1092–1099). The toxicity of individual dioxin isomers is expressed by toxic equivalency factors (TEFs), which are relative toxicity factors of the isomers compared to 2,3,7,8-TeCDD which is set as 1. The concentrations of the individual isomers are multiplied by their TEFs to calculate their toxicity. The sum of these toxicity values is the toxic equivalent (TEQ), i.e., the total toxicity of all the isomers existing in the target.

Thus the EIA system, which mainly measures 2,3,7,8-TeCDD, can not be said to be an accurate measurement system for dioxin toxicity. In particular, dioxin TEQ of exhaust gas emitted from waste incinerators, which are a main source of dioxins, is known to be highly correlated to the concentration of pentachlorinated dibenzofurans or hexachlorinated dibenzofurans rather than 2,3,7,8-TeCDD. In addition, when the analytes are exhaust gas samples, there are cases in which the measurements obtained using the conventional EIA system are significantly different from the results of instrumental analysis. Thus the use of the EIA system may be limited.

Moreover, when 2,3,7,8-TeCDD or like dioxin isomers are used as a standard in EIA, the assayer should handle a highly toxic compound for the standard preparation, resulting in the necessity of ensuring safety and involving problems such as the mental burden on the assayer.

Therefore, a non-toxic compound is desired as a standard for the quantitative determination of dioxins in samples. In this connection, Japanese Unexamined Patent Publications Nos. 128731/2002, 131316/2002 and 155023/2002 describe using a chlorophenol derivative as a standard.

DISCLOSURE OF THE INVENTION

An object of the invention is to provide a dioxin immunoassay standard that does not have a toxic equivalency factor (TEF). Another object of the invention is to provide an immunoassay method using this standard that enables simple, highly sensitive measurement of dioxin concentration or toxic equivalent in environmental samples.

To achieve the above objects, the present inventors carried out intensive research and found the following:

(i) When the concentration of dioxins in a sample is determined by immunoassay using as a standard a chlorophenol derivative of formula (1)

wherein $R^1$, $R^2$, $R^3$ and $R^4$ may be the same or different and represent chlorine or hydrogen, n is an integer from 1 to 10, and Z represents an amino acid residue or peptide, and the TEQ is calculated from the concentration, there is a high correlation between the obtained TEQ and that obtained by the official method of determining the concentration of each dioxin in a sample.

(ii) Since the above chlorophenol derivative does not have a toxic equivalency factor (TEF), the use of this compound as a dioxin assay standard enables safe calculation of dioxin concentration and toxic equivalent (TEQ) of environmental samples.

The present invention has been accomplished on the basis of the above findings. The invention provides the following:

1. A compound of formula (1)

wherein $R^1$, $R^2$, $R^3$ and $R^4$ may be the same or different and represent chlorine or hydrogen, n is an integer from 1 to 10, and Z represents an amino acid residue or peptide.

2. An immunoassay standard for dioxins comprising a compound of formula (1)

wherein $R^1$, $R^2$, $R^3$ and $R^4$ may be the same or different and represent chlorine or hydrogen, n is an integer from 1 to 10, and Z represents an amino acid residue or peptide.

3. An immunoassay kit for dioxins comprising the compound of item 1.

4. A kit according to item 3, further comprising an anti-dioxins antibody.

5. A kit according to item 3 or 4, further comprising a competitive antigen.

6. An immunoassay method for quantitative determination of dioxins, the method using the compound of item 1 as a standard.

7. An immunoassay method according to item 6 selected from the group consisting of enzyme immunoassay, radioactive immunoassay and fluoroimmunoassay.

8. An immunoassay method for determining the dioxins concentration of a sample and calculating the TEQ, the method using the compound of item 1 as a standard.

9. An immunoassay method according to claim 8 selected from the group consisting of enzyme immunoassay, radioactive immunoassay and fluoroimmunoassay.

10. An immunoassay method for dioxins comprising the following steps:
(1) reacting a sample with an anti-dioxin antibody to determine the amount of antigen reacted with the antibody; and
(2) comparing the amount of antigen reacted with the antibody in step (1) with that determined by allowing a known concentration of the compound of item 1 to react with the anti-dioxin antibody to compute the dioxins concentration in the sample.

11. An immunoassay method according to item 10 wherein the amount of antigen reacted with the antibody is determined by a method selected from enzyme immunoassay, radioactive immunoassay and fluoroimmunoassay.

The present invention provides an immunoassay standard for dioxins that does not have a toxic equivalency factor (TEF), and an immunoassay method using this standard that enables simple, highly sensitive measurement of dioxins concentration or toxic equivalent of environmental samples.

More specifically, when the dioxin concentration of a sample is quantitatively determined using the immunoassay standard of formula (1) and the TEQ is calculated therefrom, the concentration and TEQ have a good correlation with the TEQ obtained by the official method of determining the concentrations of dioxins having TEFs by instrumental analysis. The use of the compound of the invention as a standard for quantitative determination of dioxins enables accurate, highly sensitive TEQ determination of samples, allowing an accurate evaluation of dioxin toxicity compared to EIA in the prior art.

In addition, the hitherto known official method takes a long time to evaluate TEQ because TEQ is calculated by measuring the concentrations of 29 types of dioxins and computing TEQ from the concentrations. In contrast, immunoassay using the compound of the invention takes a comparatively short time to evaluate TEQ.

The standard of the invention is a compound to which the WHO has not assigned any toxic equivalency factor, thus being assumed to be a non-toxic compound. The non-toxicity is also clear from the fact that the compound of the invention is a derivative obtained by the addition of a methylene chain and a peptide to a commercially available chlorophenol compound (for example, 2,4,5-trichlorophenol). The use of the compound of the invention can therefore greatly enhance safety in dioxin immunoassay.

As shown above, the compound and the immunoassay method of the invention find wide application in environmental analysis and the like and are also useful in the analysis of biological samples such as foods, mothers' milks, blood and urine.

DISCLOSURE OF THE INVENTION

The present invention will be described below in detail.

(I) Compound of the Invention

Basic Construction

The compound of the following formula (1) is a novel compound not described in any publication:

(1)

wherein $R^1$, $R^2$, $R^3$ and $R^4$ may be the same or different and represent chlorine or hydrogen, n is an integer from 1 to 10, and Z represents an amino acid residue or peptide.

Preferable Compounds

Although the compound of formula (1) is not particularly limited in the number and position of chlorine substituents, it is preferable, in view of the reactivity with anti-dioxin antibodies, that the total number of chlorine substituents in the compound is 3 or more, and preferably 3.

Among the compounds whose total number of chlorine substituents is 3, preferable compounds are those wherein $R^1$ and $R^2$ are chlorine and $R^3$ and $R^4$ are hydrogen; those wherein $R^1$ and $R^3$ are chlorine and $R^2$ and $R^4$ are hydrogen; those wherein $R^2$ and $R^3$ are chlorine and $R^1$ and $R^4$ are hydrogen; those wherein $R^2$ and $R^4$ are chlorine and $R^1$ and $R^3$ are hydrogen; and those wherein $R^3$ and $R^4$ are chlorine and $R^1$ and $R^2$ are hydrogen. Particularly preferable are compounds wherein $R^2$ and $R^3$ are chlorine and $R^1$ and $R^4$ are hydrogen; and those wherein $R^2$ and $R^4$ are chlorine and $R^1$ and $R^3$ are hydrogen. The most preferable are compounds wherein $R^2$ and $R^4$ are chlorine and $R^1$ and $R^3$ are hydrogen.

Preferably, n is an integer from about 0 to 20, particularly an integer of about 2 to 6, and most preferably 2. When the length of polymethylene chain, n, is within this range, synthesis is facilitated.

The amino acid residue or peptide represented by Z is not particularly limited so long as the peptide is composed of 100 or less amino acid residues according to the usual definition of peptide. An amino acid residue or peptide having about 1 to 50 residues, particularly about 1 to 10 residues, more particularly about 1 to 4 residues, further particularly about 1 to 3 residues, is preferable. Excessively long peptides have increased water solubility and are thus difficult to dissolve in organic solvents at the time of measurement and may result in precipitation in the reaction mixture. Such a problem does not arise so long as the number of amino acid residues is within the above-mentioned range.

Specific examples of preferable compounds are those wherein $R^1$ and $R^2$ are chlorine and $R^3$ and $R^4$ are hydrogen, n is an integer from 2 to 6, and Z is a peptide having about 1 to 4 amino acid residues: those wherein $R^1$ and $R^3$ are chlorine and $R^2$ and $R^4$ are hydrogen, n is an integer from 2 to 6, and Z is a peptide having about 1 to 4 amino acid residues; those wherein $R^2$ and $R^3$ are chlorine and $R^1$ and $R^4$ are hydrogen, n is an integer from 2 to 6, and Z is a peptide having about 1 to 4 amino acid residues; those wherein $R^2$ and $R^4$ are chlorine and $R^1$ and $R^3$ are hydrogen, n is an integer from 2 to 6, and Z is a peptide having about 1 to 4 amino acid residues; and those wherein $R^3$ and $R^4$ are chlorine and $R^1$ and $R^2$ are hydrogen, n is an integer from 2 to 6, and Z is a peptide having about 1 to 4 amino acid residues.

Among these, preferable compounds are those wherein $R^2$ and $R^3$ are chlorine and $R^1$ and $R^4$ are hydrogen, n is an integer from 2 to 6, and Z is a peptide having about 1 to 4 amino acid residues; and those wherein $R^2$ and $R^4$ are chlorine and $R^1$ and $R^3$ are hydrogen, n is an integer from 2 to 6, and Z is a peptide having about 1 to 4 amino acid residues.

Particularly preferable compounds are those wherein $R^2$ and $R^4$ are chlorine and $R^1$ and $R^3$ are hydrogen, n is 5, and Z is an amino acid or peptide having about 1 to 3 amino acid residues; and those wherein $R^2$ and $R^3$ are chlorine and $R^1$ and $R^4$ are hydrogen, n is 2, and Z is an amino acid or peptide having about 1 to 3 amino acid

Use

The compound of formula (1) reacts with an anti-dioxin antibody and thus can be used as an immunoassay standard for dioxins. Since this compound does not have a toxic equivalency factor (TEF), the use of the compound enables the establishment of an immunoassay system for dioxins that allows safe measurement.

Production Method

The dioxins immunoassay standard of the invention can be synthesized, for example, by the following method, although the method is not limited thereto.

The compound of formula (2)

(2)

wherein $R^1$, $R^2$, $R^3$ and $R^4$ may be the same or different and represent chlorine or hydrogen, and n is an integer from 1 to 10, is activated by an activated ester method which comprises reacting the compound with N-hydroxysuccinimide to give an activated ester compound of formula (3)

wherein $R^1$, $R^2$, $R^3$ and $R^4$ may be the same or different and represent chlorine or hydrogen, and n is an integer from 1 to 10.

The compound of formula (3) is then reacted with an amino group-containing compound such as an amino acid or a peptide according to an ordinary method to give a compound of formula (1).

The chlorophenol derivative of formula (2) used as the starting compound can be synthesized, for example, by the following method. Chlorophenol, potassium carbonate and ethyl 6-bromohexanoate are stirred at 60° C. for 16 hours. After completion of the reaction, the reaction mixture is extracted with ethyl acetate. The extract is concentrated under reduced pressure and the residue is dissolved in ethanol. After addition of sodium hydroxide solution, the mixture is stirred at room temperature for 3 hours. After completion of the reaction, the reaction mixture is neutralized with concentrated hydrochloric acid and concentrated under reduced pressure. The resulting mixture is acidified by addition of concentrated hydrochloric acid, extracted with ethyl acetate, and recrystallized to give a chlorophenol derivative compound of formula (2).

(II) Dioxins Immunoassay Kit

The dioxins immunoassay kit of the invention comprises the compound of formula (1) of the invention as a standard for dioxins quantitative determination. The anti-dioxin antibody may be prepared by the user or may be contained in the kit. A kit containing the antibody is convenient. The anti-dioxin antibody will be described later in another section. For competitive immunoassay, the kit may further comprise a competitive antigen. The competitive antigen will also be described later in another section.

The kit may further comprise other items such as a reaction vessel, a blocking agent for masking the free surface of the vessel, a buffer, a secondary antibody for indirect competitive immunoassay and the like.

(III) Dioxin Immunoassay Method

Basic Construction

The method of the invention is an immunoassay for dioxins quantitative determination using the compound of formula (1) as a standard. More specifically, the method of the invention is an immunoassay for calculating the concentration of dioxins in a sample, or for calculating the concentration of dioxins and further computing the TEQ, the method using the compound of formula (1) as a standard.

The dioxins immunoassay of the invention comprises the following steps:

(1) reacting a sample with an anti-dioxin antibody to determine the amount of antigen reacted with the antibody; and (2) comparing the amount of antigen reacted with the antibody in step (1) with that determined by allowing a known concentration of the compound of formula (1) to react with the anti-dioxin antibody to compute the concentration of dioxins in the sample.

The dioxins immunoassay of the invention is characterized by using the chlorophenol derivative of formula (1) as a standard for dioxins immunoassay and can be carried out using this standard in a similar manner as usual immunoassay.

The compound of the invention is applicable to any known immunoassay method. Examples of such known immunoassay methods include enzyme immunoassay (EIA), radioimmunoassay (RIA), fluorescence immunoassay (FIA), and the like. EIA is preferable in view of its simplicity of measurement.

EIA includes competitive immunoassay, non-competitive immunoassay, homogeneous immunoassay, etc. Since dioxins are low molecular weight compounds, competitive assays may be usually used. Competitive immunoassay includes indirect competitive assays in which an antigen is immobilized on microplate wells, tubes or the like, and direct competitive assays in which an antibody is immobilized on microplate wells, tubes or the like.

Indirect Competitive Assay (i) Competitive Antigen

In indirect competitive assays, a dioxin or a complex of dioxin and carrier protein is used as a competitive antigen immobilized on wells. When the reaction vessel is an untreated vessel made of resin, glass or the like, a complex of dioxin and carrier protein is preferably used because it is difficult to immobilize a dioxin alone on the surface of the vessel. In the case of using a reaction vessel whose surface is activated by a highly reactive functional group such as an amino group or a carboxyl group, dioxin alone can be immobilized via the functional group on the vessel. Irrespective of the use of carrier proteins, linkers are preferably attached to dioxins, whereby steric hindrance is alleviated and the reactivity of the competitive antigen with the anti-dioxin antibody improves, resulting in enhanced assay sensitivity for dioxins in a sample.

Examples of usable dioxins include polychlorinated dibenzo-p-dioxins (PCDDs), polychlorinated dibenzofurans (PCDFs) and coplanar polychlorinated biphenyls (Co-PCBs). By using a dioxin or a dioxin-like compound having little similarity to toxic dioxins, reactivity of the anti-dioxin antibody with the competitive antigen is less than with the dioxins in a sample, resulting in improved detection sensitivity of the dioxins concentration in the sample.

The carrier protein is not particularly limited and any known carrier proteins can be used. Examples of carrier proteins include KLM (Keyhole limpet hemocyanin), bovine serum albumin (BSA) and the like.

The linker is preferably one that does not sterically hinder binding with the antibody nor adversely affect solubility in the reaction process. Examples of usable linkers include polymethylene chains and the like. The linker is disposed between the dioxins or dioxins-like compound and the container or between the carrier protein complex of the dioxin or dioxin-like compound and the container.

Highly sensitive quantitative determination of dioxins can be achieved by using the chlorophenol derivative of formula (1) of the invention as a competitive antigen. It is particularly preferable that the competitive antigen be the same compound as the standard for the calibration curve preparation. In this case, an antigen to be immobilized can be produced by replacing the amino acid or peptide moiety at an end of the substituted compound of the standard represented by formula (1) with a carrier protein such as BSA.

(ii) Anti-dioxin Antibody

The antibody used in EIA can be prepared by a known method comprising haptenizing a dioxin such as polychlorinated dibenzo-p-dioxin (PCDD), polychlorinated dibenzofuran (PCDF) or coplanar polychlorinated biphenyl (Co-PCB), conjugating the hapten to a carrier protein such as BSA and immunizing a mammal using the conjugate as an immunization antigen (Kun Chae, et al., J. Agric. Food., 25, 1207–1209 (1977); Simona G. Merica, et al., Can. J. Chem., 73, 826–834 (1995)).

The antibody may be monoclonal or polyclonal and is not especially limited. The use of a monoclonal antibody is preferable in view of antibody homogeneity and unlikelihood of lot-to-lot differences in antibody production. The monoclonal antibody is an antibody obtained from single antibody-producing cells that are prepared by cloning a hybridoma produced by the fusion of a haptenized dioxins-immunized mouse spleen cell with a tumor cell. Any monoclonal antibody that recognizes dioxins can be used.

The indirect competitive assay can be carried out, for example, in the following manner. First, the competitive antigen is immobilized on the surface of the wells of a reaction vessel such as a microplate. Then the portion of the surface of the wells to which the antigen is not attached is blocked with a commercially available blocking agent such as bovine serum albumin, casein or the like. A sample and a primary antibody (anti-dioxin antibody) is added to the wells, and the sample and the immobilized antigen are allowed to competitively interact with the antibody. Antibodies not bound to the immobilized antigen are removed by washing. Then a secondary antibody, for example, an enzyme-labeled antibody prepared by labeling a goat anti-mouse immunoglobulin antibody with peroxidase (HRP), alkaline phosphatase (ALP) or like enzyme, is added to the wells and allowed to bind to the primary antibody binding to the immobilized antigen. After the resulting antibody conjugate is washed with buffer several times, the substrate for the labeled enzyme is added and absorbance of the colored enzymatic reaction product is measured. When the enzyme is peroxidase, hydrogen peroxide may be used as a substrate, and o-phenylenediamine or tetramethylbenzidine may be used as the coloring agent. When the enzyme is alkaline phosphatase, p-nitrophenylphosphoric acid is usually used as a substrate.

In the above competitive assay, the percentage of inhibition by a sample is obtained by determining the percent absorbance decrease by addition of a test sample relative to the absorbance of the sample-free reaction mixture. Using the compound of formula (1) as a dioxin standard, a competitive reaction is carried out in the same manner except using several known concentrations of the standard solution in place of the sample to prepare a calibration curve relating the standard solution concentrations and the percentage of inhibition. The dioxins concentration in the sample is calculated in terms of standard solution concentration by comparing the calibration curve and the percentage of inhibition.

Direct Competitive Immunoassay

In direct competitive immunoassay, the anti-dioxin antibody is immobilized on the surface of the wells of a reaction vessel and the portion of the surface of the wells to which the antigen is not bound are blocked in the same manner as above. By adding a competitive enzyme-labeled antibody and a test sample to the wells, the sample and the enzyme-labeled antigen are allowed to competitively interact with the immobilized antibody. The enzyme-labeled antigen not bound to the antibody is then removed by washing and the substrate for the labeling enzyme is added to determine the absorbance of the reaction product.

The enzyme-labeled antigen can be prepared by linking peroxidase, alkaline phosphatase or like enzyme to the same dioxin or dioxin-like compound used as a competitive antigen in indirect competitive immunoassay. When using an antigen prepared by replacing the amino acid or peptide moiety at an end of the compound of formula (1) with an enzyme such as peroxidase or alkaline phosphatase, sensitivity is enhanced.

When RIA is carried out instead of EIA, a labeled antigen can be prepared by labeling the dioxins or dioxins-like compound with an isotope. When FIA is carried out, a labeled antigen can be prepared by attaching a fluorescent substance such as rhodamine or a chemiluminescent substance to the dioxins or dioxins-like compound.

Test Sample

The sample type is not specifically limited and may include, for example, environmental samples collected from the environment, biological samples, foods and like various products, and dioxin solutions prepared for experiments. The method of the invention is especially suitable for environmental samples for use as test samples. Examples of environmental samples include air; exhaust gases from automobiles, machines and devices, factories, and the like; soils; river, lake, harbor or port waters; combustion or fly ashes and the like. Biological samples include mothers' milk, blood and urine.

TEQ Calculation Method

The test sample may be directly subjected to immunoassay or may be pretreated to extract a fraction containing large amounts of dioxin therefrom. Performing a pretreatment is preferable. Examples of pretreatment methods are given below, but are not limiting.

(i) Exhaust Gas Sample

A gas sample of A $Nm^3$ is collected and the substances contained therein are extracted with toluene. The extract is measured to 20 ml and it is referred to as a crude extract. 10 ml of the extract is treated with sulfuric acid until the sulfuric acid layer becomes colorless. The treated extract is dissolved in hexane and cleaned up by applying it to a multilayered silica gel column comprising layers of 1 g of sodium sulfate, 1 g of 10% silver nitrate silica gel and 3 g of silica gel with 200 ml of hexane. 1 ml of a DMSO solution containing this extract is subjected to immunoassay.

The obtained dioxins concentration in terms of the standard, hereinafter simply referred to as "Standard dioxins concentration", is inserted into the following equation to calculate toxicity equivalent (TEQ):

$$TEQ(\text{ng-}TEQ/Nm^3) = 0.0922 \times \text{Standard dioxins concentration } (\mu g/Nm^3)^{0.8474}$$

In the above formula, 0.0922 and 0.8474 are coefficients in the correlation equation between the dioxins concentration in exhaust gases determined by the method of this invention in the Example and the dioxins TEQ obtained by the official method. These are constants assigned to each type of sample. Unit conversion of the Standard dioxins concentration can be done by the following formula:

$$\text{Standard dioxins concentration } (\mu g/N\,m^3) = \text{Standard dioxins concentration } (ng/ml) \times 1/10 \times 20 \times 1/A \times 1/1000$$

(ii) Fly Ash

Fly ashes (B g) are collected and the compounds contained therein are extracted with toluene. The extract is measured to 20 ml and it is referred to as a crude extract. 1 ml of the extract is measured out and cleaned up. 2 ml of a DMSO solution containing this extract is subjected to immunoassay.

The obtained Standard dioxins concentration is inserted into the following equation to calculate toxicity equivalent (TEQ):

$$TEQ(\text{ng-}TEQ/g) = 0.0038 \times [\text{Standard dioxins concentration } (\mu g/g)]^{0.9796}$$

In the above formula, the values 0.0038 and 0.9796 are coefficients in the correlation equation between the dioxins concentration in fly ashes determined by the method of this invention in the Example and the dioxin TEQ obtained by the official method. These values are constants assigned to each type of sample.

Unit conversion of the Standard dioxins concentration can be done by the following formula:

$$\text{Standard dioxins concentration } (\mu g/g) = \text{Standard dioxins concentration } (\text{ng/ml}) \times 2/1 \times 20 \times 1/B \times 1/1000$$

(iii) Soil

Soil (B g) is collected and the compounds contained therein extracted with toluene. The extract is measured to 20 ml and it is referred to as a crude extract. 1 ml of the crude extract is measured out and cleaned up. 2 ml of a DMSO solution containing this extract is subjected to immunoassay. The obtained Standard dioxins concentration is inserted into the following equation to calculate toxicity equivalent (TEQ):

$$TEQ(\text{ng-}TEQ/g) = 9.4553 \times [\text{Standard dioxins concentration } (\mu g/g)]^{0.9352}$$

In the above formula, the values 9.4553 and 0.9352 are coefficients in the correlation equation between the dioxins concentration in fly ashes determined by the method of this invention in the Example and the dioxins TEQ obtained by the official method. These values are constants assigned to each type of sample. Unit conversion of the Standard dioxins concentration can be done in the same manner as in fly ashes.

EXAMPLES

Examples are given below to illustrate the invention in more detail. The scope of the invention is not limited to these examples.

Example 1

Preparation of Dioxins Immunoreaction Assay Standard

Of the compounds of formula (1) of the invention, a compound in which $R^2$ and $R^4$ are chlorine and $R^1$ and $R^3$ are hydrogen was synthesized by the following method. The synthetic procedure is described with reference to FIG. 1.

Figure 1:
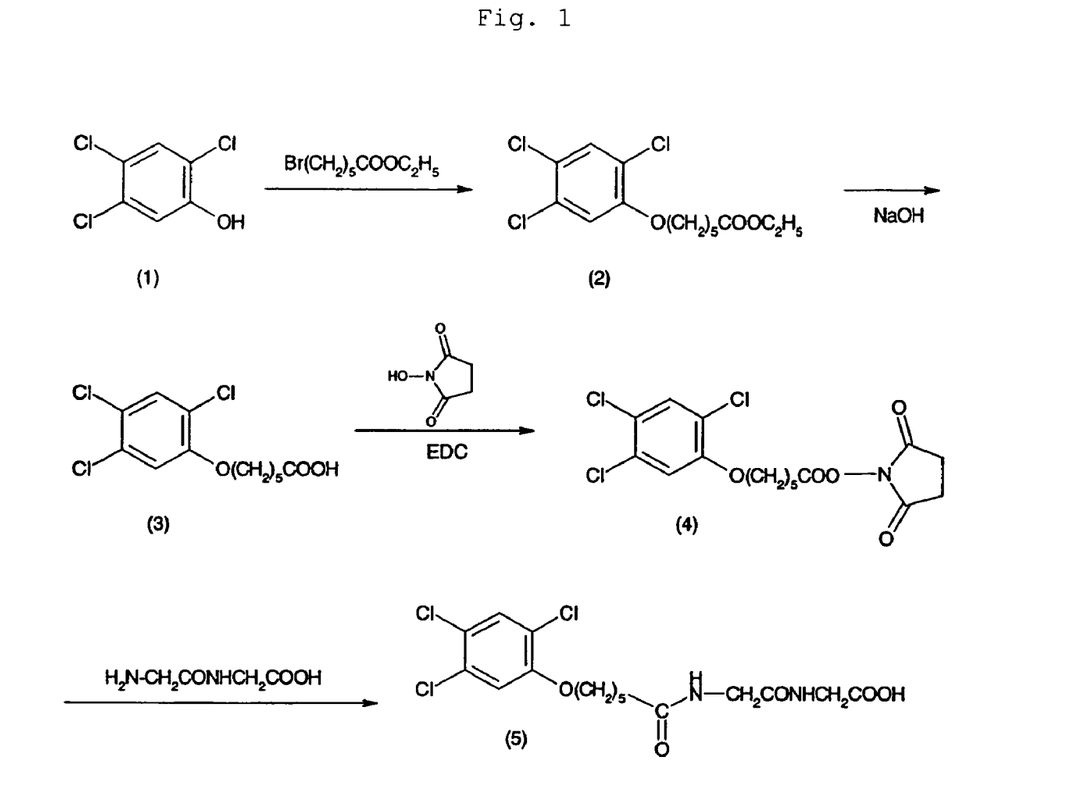
FIG. 1 shows a synthetic scheme for the dioxins immunoassay standard of Example 1.

Under argon gas, 15.0 g (76.0 mmol) of 2,4,5-trichlorophenol (1) (commercially available product), 18.6 g (83.6 mmol) of ethyl 6-bromohexanoate, 12.60 g (91.2 mmol) of potassium carbonate, and 150 ml of anhydrous dimethylformamide were mixed and heated with stirring at 60° C. overnight. After completion of the reaction, the reaction mixture was cooled to room temperature. After addition of 450 ml of water, the reaction mixture was extracted with 225 ml of ethyl acetate twice. The extract was dried over magnesium sulfate, the desiccant was filtered off and the organic layer was concentrated to give 30.7 g of a pale yellow oil as a crude product. The crude product was purified by silica gel column chromatography (silica gel: 450 g, eluant: ethyl acetate/n-hexane=1:15) to give 26.5 g of ethyl 6-(2,4,5-trichlorophenoxy)hexanoate (2) as a transparent oil (100% yield).

The ethyl 6-(2,4,5-trichlorophenoxy)hexanoate was dissolved in 200 ml of ethanol and then 200 ml of 2N aqueous sodium hydroxide solution was added dropwise with ice-cooling and stirred at room temperature for 3 hours. After completion of the reaction, the reaction mixture was neutralized with 70 ml of concentrated hydrochloric acid and concentrated to half its original volume. The concentrated reaction mixture was acidified by addition of 5 ml of concentrated hydrochloric acid and extracted with 100 ml of ethyl acetate once and with 150 ml of ethyl acetate twice. The organic layer was washed with 200 ml of water and then with 200 ml of saturated aqueous sodium chloride solution and dried over magnesium sulfate. After filtering off the desiccant, the organic layer was concentrated to give 23.3 g of a white solid as a crude product. After addition of 25 ml of isopropyl ether and 50 ml of n-hexane, the crude product was recrystallized. The precipitated crystals were collected by filtration and washed with isopropyl ether/n-hexane (isopropyl ether/n-hexane=1:3) to give 6-(2,4,5-trichlorophenoxy)hexanoic acid (3) as white crystals (88.0% yield). 18.2 g (58.4 mmol) of 6-(2,4,5-trichlorophenoxy)hexanoic acid (3) was dissolved in 180 ml of methylene chloride and then 12.7 g (70.1 mmol) of 1-ethyl-3-(3'-diethylaminopropyl)carbodiimide hydrochloride and 8.07 g (70.1 mmol) of N-hydroxysuccinimide were added, followed by stirring at room temperature overnight. After completion of the reaction, the reaction mixture was added to 1250 ml of THF. The organic layer was successively washed with 360 ml of water, 540 ml of saturated aqueous sodium hydrogen carbonate solution and 540 ml of water and dried over sodium sulfate. After filtering off the desiccant, the organic layer was concentrated to give 21.9 g of a white solid as a crude product. The crude product was purified by silica gel column chromatography (using 400 g of silica gel and methylene chloride as eluant for the first chromatographic step; using 330 g of silica gel and methylene chloride as eluant for the second chromatographic step) to give 9.73 g of succinimidyl 6-(2,4,5-trichlorophenoxyl)hexanoate (4) as a white solid (40.7% yield).

20 mg of succinimidyl 6-(2,4,5-trichlorophenoxyl)hexanoate (4) was dissolved in 100 ml of dimethyl sulfoxide. Then 100 ml of 50 mM aqueous glycylglycine solution was gradually added and stirred at room temperature for 3 hours to give an immunoassay standard solution for dioxins.

A compound of formula (1) in which $R^2$ and $R^3$ are chlorine and $R^1$ and $R^4$ are hydrogen was synthesized in the same manner as above except that 2,4,6-trichlorophenol (commercially available product) was used as a starting compound in place of 2,4,5-trichlorophenol.

In addition, a compound of formula (1) in which $R^1$ and $R^4$ are chlorine and $R^2$ and $R^3$ are hydrogen was synthesized in the same manner as above except that 3,4,5-trichlorophenol (commercially available product) was used as a starting material in place of 2,4,5-trichlorophenol.

Example 2

Preparation of Competitive Assay Antigen

A competitive assay antigen was prepared using succinimidyl 6-(2,4,5-trichlorophenoxyl)hexanoate (4) obtained in Example 1 and bovine serum albumin (BSA). More specifically, first, 545.5 µl of dimethyl sulfoxide was added to 1 ml of a bovine serum albumin (BSA) solution in 50 mM phosphate buffer (pH 8.0) (corresponding to 15 mg ($2.27 \times 10^{-7}$ mol of BSA)) with stirring while being cooled with ice. Then 454.5 µl (40 equivalents ($9.09 \times 10^{-6}$ mol)) of succinimidyl 6-(2,4,5-trichlorophenoxyl)hexanoate (BB2-4) was added dropwise and allowed to react at room temperature for 1 hour. After the reaction, 4L of PBS was dialyzed to give a competitive assay antigen.

Example 3

Preparation of Exhaust Gas Sample and Determination of Dioxins TEQ by the Official Method Exhaust gas emitted from a waste incineration facilities was collected and the dioxins concentration of the sample was determined using a high performance gas chromatography-mass spectrometer (GC-MS) according to JIS K0311 (the official method). In addition, about 3 $Nm^3$ of exhaust gas was sucked from the flue of a city waste incineration facilities using a gas sampling device and the sample was extracted with an organic solvent such as toluene or dichloromethane, selected in accordance with the form such as filter paper, resin or absorbent liquid. These extracts were combined and concentrated to 20 ml to give a crude extract.

1 ml was measured out of the crude extract and purified by sulfuric acid treatment, multilayered silica gel chromatography, and activated carbon column chromatography. The concentrations of dioxin isomers were determined using a gas chromatography-mass spectrometer (product of Micromass).

The concentrations of the dioxin isomers were then multiplied by their TEFs to obtain the dioxins TEQ of the exhaust gas sample.

In the meantime, another 1 ml of the crude extract was measured out and purified by sulfuric acid treatment and multilayered silica gel chromatography. After evaporating organic solvent, the residue was dissolved in 2 ml of dimethyl sulfoxide (DMSO) and used as an EIA evaluation sample.

Example 4

TEQ Determination of Exhaust Gas Sample Using Anti-dioxins Monoclonal Antibody by Indirect Competitive Assay A competitive assay antigen prepared in Example 2 was dissolved in PBS to a concentration of about 1 µg/ml, and 100 µl of this solution was pipetted into each well. The plate was hermetically sealed and allowed to stand at 4° C. for 18 hours to solidify the solution. After removal of the antigen solution, the plate was washed with 0.05% Tween 20-containing PBS three times and 300 µl of a 5-fold diluted blocking solution (product of Nacalai Tesque Co.) was pipetted into each well. The plate was hermetically sealed and allowed to stand at 4° C. overnight for blocking, thus giving a immunoassay plate for dioxins. Using this plate, dioxins immunoassay was performed in the following manner.

The dioxins standard prepared in Example 1 was diluted with 50% DMSO containing 0.01% Triton X100 to produce a dilution series ranging from 0 to 0.2 µg/ml. The exhaust gas sample prepared in Example 3 was dissolved in DMSO and diluted with 50% DMSO containing 0.01% Triton X100 to give an assay sample.

In the meantime, a hybridoma that produces an anti-dioxins monoclonal antibody was cultured in a serum-free medium in a $CO_2$ incubator at 37° C. for 1 week or more and the culture supernatant thus obtained was purified by affinity chromatography using a protein A column and dialyzed in PBS to provide an anti-dioxins monoclonal antibody.

50 µg of each of the dilution series of the dioxins standard and the exhaust gas sample were added to the dioxins assay plate and 50 µl of an anti-dioxins monochronal antibody solution that had been diluted with PBS containing 0.2% BSA to a concentration of 0.1 µg/ml was added to each well and allowed to react at 4° C. for 1 hour. After the reaction, the solution added to each well was removed and the plate was washed with PBS containing 0.005% Tween 20 three times. Then 100 µl of a goat anti-mouse IgG(H+L) HRP labeled antibody (obtained by affinity purification, product of DAKO) diluted 2000-fold with PBS containing 0.2% BSA was pipetted into each well. The plate was allowed to stand at room temperature for 1 hour and washed with PBS containing 0.05% Tween 20 three times. Then 100 µl of HRP substrate TMB (product of BioFX) was pipetted into each well and allowed to stand at room temperature for 30 minutes. After addition of 100 µl of 0.5M sulfuric acid solution to each well, absorbance was measured at a wavelength of 455 nm (655 nm for control) using a microtiter spectrophotometer.

A standard curve (calibration curve) was prepared from absorbance data obtained using the dioxins standard. Absorbance data obtained using the exhaust gas sample was compared and fitted to the calibration curve to determine the amount of dioxins in the sample in terms of standard substance concentration.

Figure 2:
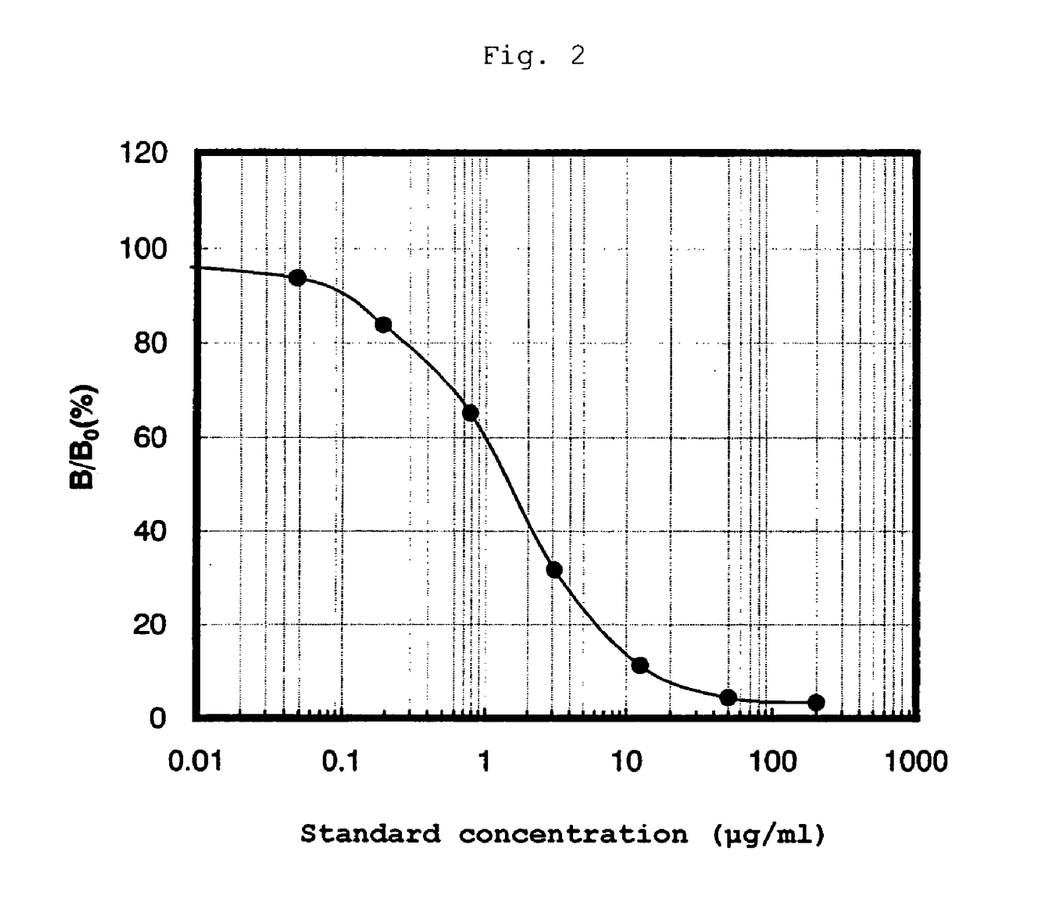
FIG. 2 shows a standard curve obtained using an embodiment of the dioxins immunoassay standard of the invention.

FIG. 2 shows the obtained standard curve. In FIG. 2, B represents absorbance in the presence of the standard, and $B_0$ represents absorbance in the absence of the standard.

Figure 3:
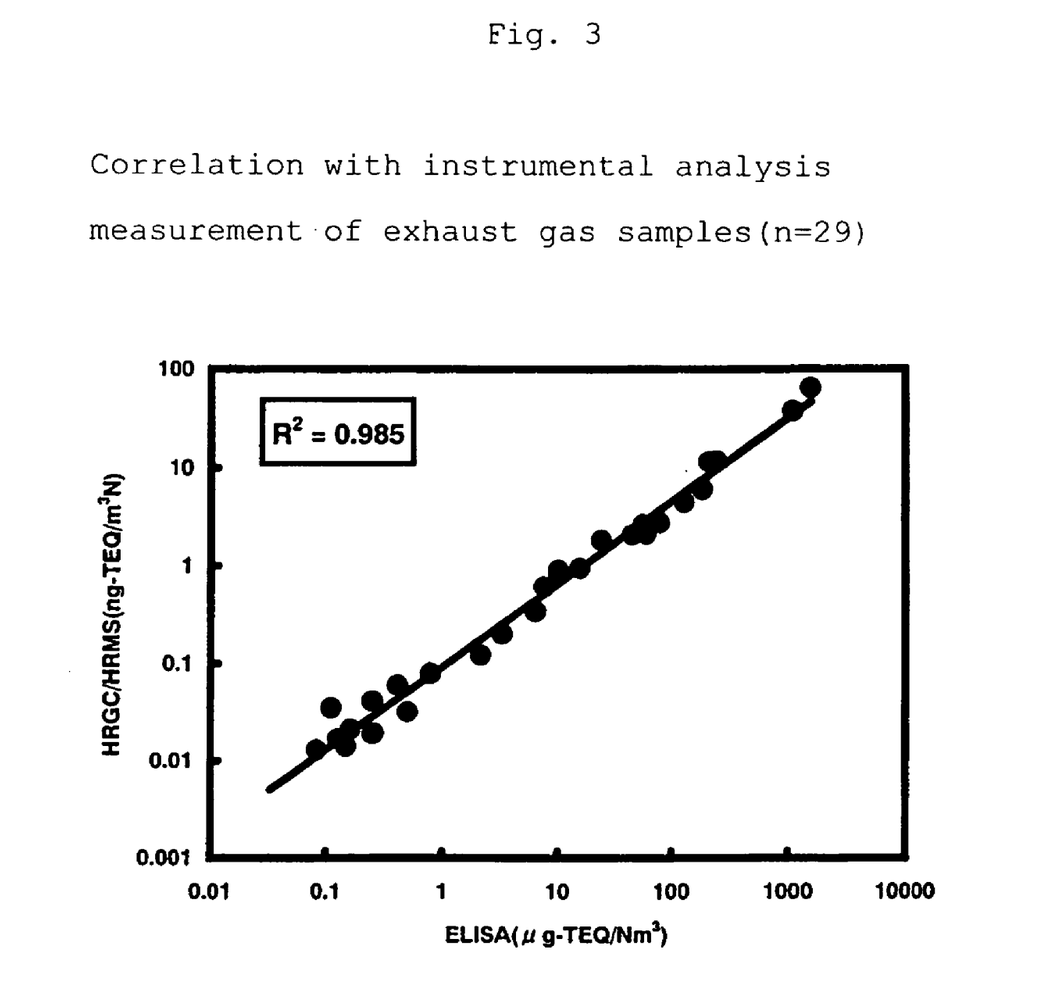
FIG. 3 shows the correlation between dioxins TEQ of exhaust gas obtained by gas chromatography-mass spectrometry and dioxins concentration of the exhaust gas obtained by performing immunoassay using the dioxins immunoassay standard of the invention.

FIG. 3 shows the correlation between dioxins TEQ obtained by quantitative determination using GC-MS in Example 3 and dioxins concentration in the sample obtained by performing immunoassay using the standard of the invention in Example 4. As is clear from FIG. 3, there is a good correlation between the measurement obtained by immunoassay of exhaust gas samples using the immunoassay standard of the invention and dioxins TEQ calculated by the official instrumental analysis method ($R^2=0.985$).

Example 5

Preparation of Fly Ash Sample and Dioxins TEQ Determination by the Official Method TEQ in fly ash samples was calculated from the results of GC-MS in the same manner as in Example 3.

Example 6

TEQ Determination of Fly Ash Sample Using Anti-dioxins Monoclonal Antibody by Indirect Competitive Assay Dioxin TEQ of fly ash samples was determined by EIA in the same manner as in Example 4.

Figure 4:
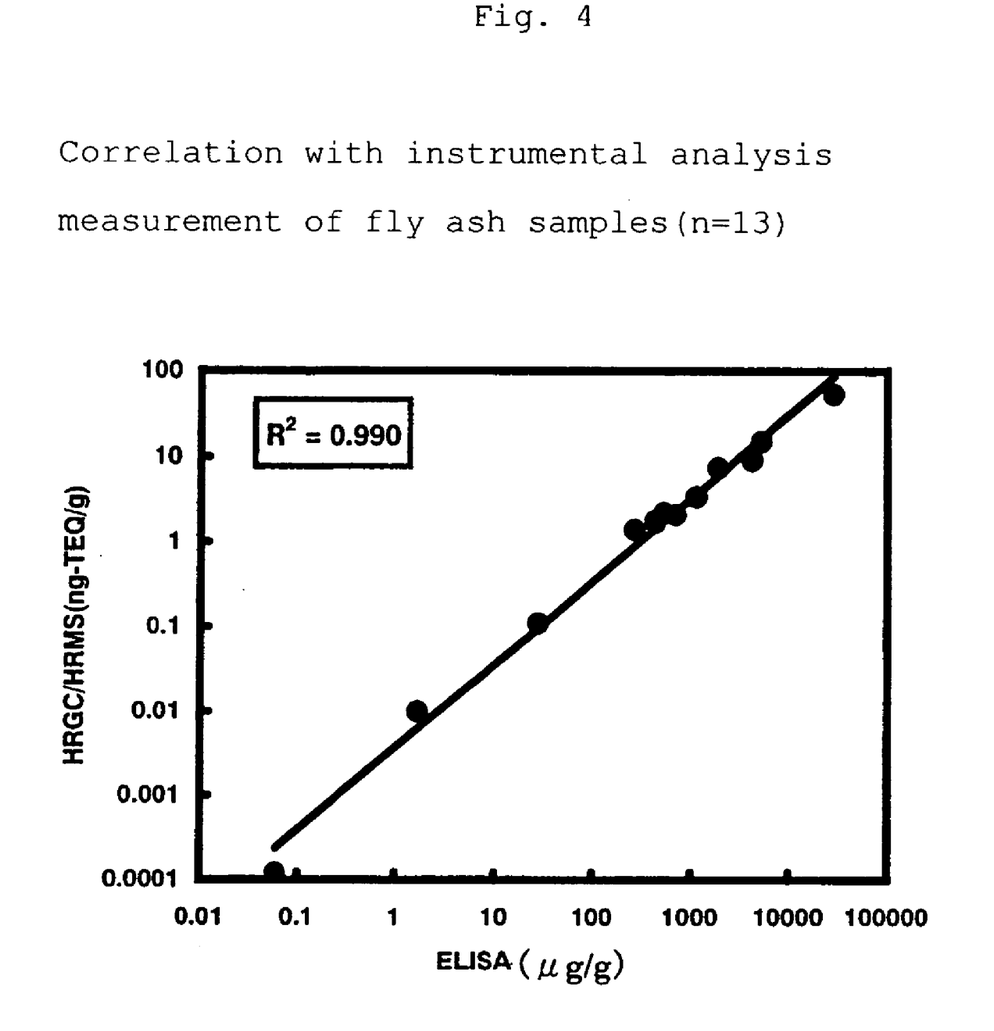
FIG. 4 shows the correlation between dioxins TEQ of fly ash obtained by gas chromatography-mass spectrometry and dioxins concentration of the fly ash obtained by performing immunoassay using the dioxins immunoassay standard of the invention.

FIG. 4 shows the correlation between dioxins TEQ obtained by quantitative determination using GC-MS in Example 5 and dioxins concentration of the sample obtained by performing immunoassay using the standard of the invention in Example 6. As is clear from FIG. 4, there is a good correlation between the measurement obtained by immunoassay of the fly ash samples using the immunoassay standard of the invention and dioxins TEQ calculated by the official instrumental analysis method ($R^2=0.990$).

Example 7

Preparation of Soil Sample and Determination of Dioxins TEQ by the Official Method TEQ in soil samples was calculated from the results of GC-MS analysis in the same manner as in Example 3.

Example 8

TEQ Determination of Soil Sample Using Anti-Dioxins Monoclonal Antibody by Indirect Competitive Assay Dioxin TEQ of soil samples was determined by EIA in the same manner as in Example 4.

Figure 5:
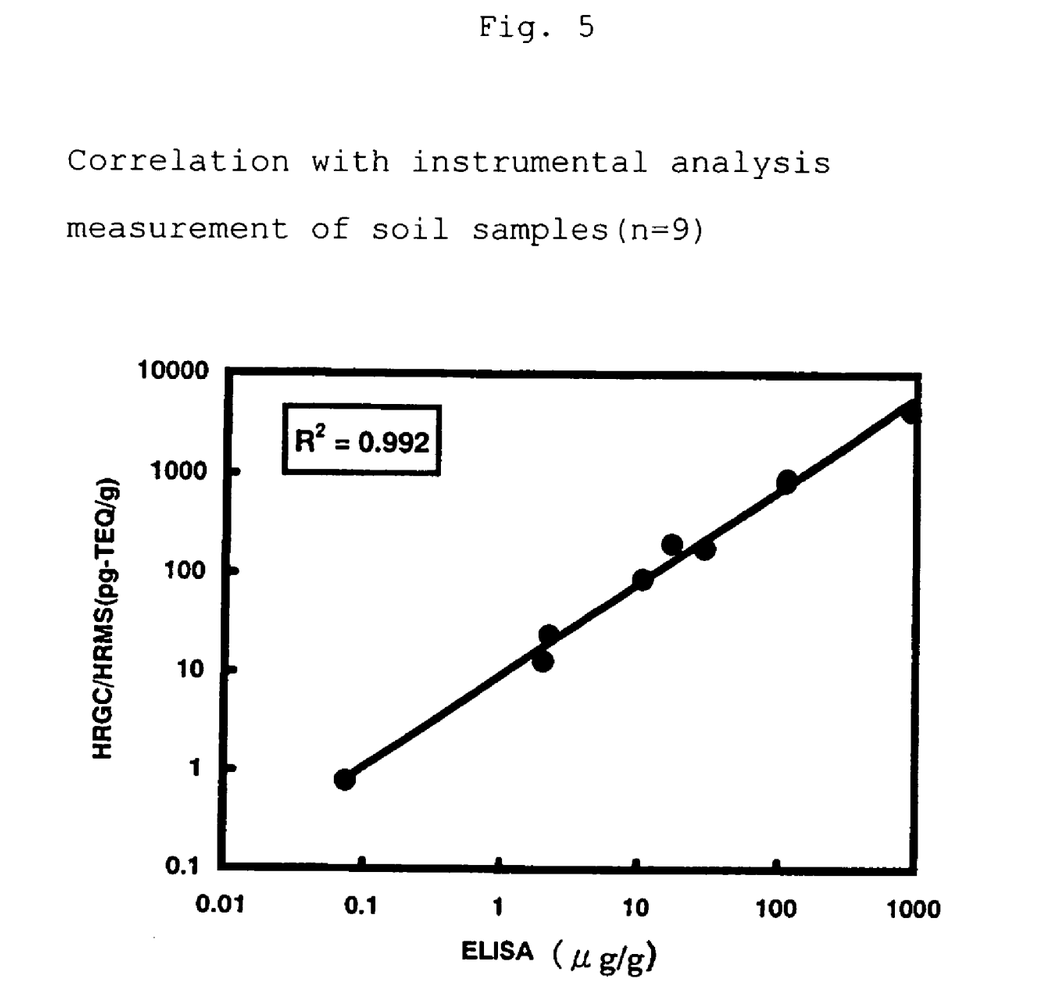
FIG. 5 shows the correlation between dioxins TEQ of soil obtained by gas chromatography-mass spectrometry and dioxins concentration of the soil obtained by performing immunoassay using the dioxins immunoassay standard of the invention.

FIG. 5 shows the correlation between dioxins TEQ obtained by quantitative determination using GC-MS in Example 7 and dioxins concentration of the sample obtained by performing immunoassay using the standard of the invention in Example 8. As is clear from FIG. 5, there is a good correlation between the measurement obtained by immunoassay of the soil samples using the immunoassay standard of the invention and dioxins TEQ calculated by the official instrumental analysis method ($R^2=0.992$).

In the above, the correlation with the official method was discussed regarding a compound of formula (1) wherein $R^2$ and $R^4$ are chlorine and $R^1$ and $R^3$ are hydrogen. Using a compound of formula (1) wherein $R^2$ and $R^3$ are chlorine and $R^1$ and $R^4$ are hydrogen and a compound of formula (1) wherein $R^1$ and $R^4$ are chlorine and $R^2$ and $R^3$ are hydrogen, the same procedure as in Examples 2 to 8 was repeated. There was also a high correlation with these compounds to the official method for dioxins TEQ.

INDUSTRIAL APPLICABILITY

The compound and method of the invention are suitable for quantitative determination of dioxins in environmental samples such as soil, air, exhaust gases, lake and river waters; biological samples such as mothers' milk, blood and urine; and products such as foods.

The invention claimed is:

1. An immunoassay method for determining the concentration of dioxins in a sample, the method comprising the following steps:
   1) allowing target dioxins in the sample and
   a competitive antigen
   to competitively react with a primary anti-dioxin antibody capable of binding to the target dioxins, and
   determining the amount of competitive antigen-antibody complex from a label incorporated into a secondary antibody binding to the primary antibody;
   2) allowing the competitive antigen and
   a compound of formula (1) of known concentration (1)

wherein $R^1$, $R^2$, $R^3$ and $R^4$ may be the same or different and each represents chlorine or hydrogen, n is an integer from 1 to 10, and Z represents 1 to 100 amino acid residues
   to competitively react with the primary anti-dioxin antibody, and
   determining the amount of competitive antigen-antibody complex from a label incorporated into a secondary antibody binding to the primary antibody;
   3) preparing a calibration curve using the amount of competitive antigen-antibody complex determined in step 2); and
   4) comparing the amount of competitive antigen-antibody complex determined in step 1) with the calibration curve prepared in step 3).

2. The immunoassay method according to claim 1, wherein the competitive antigen is a compound of formula (1) wherein Z is a carrier protein.

3. The immunoassay method according to claim 1, wherein the label is an enzyme, a radioactive substance, or a fluorescent substance.

4. The immunoassay method according to claim 1, wherein in formula (1), $R^2$ and $R^4$ are chlorine, $R^1$ and $R^3$ are hydrogen, n is 5, and Z represents 1 to 3 amino acid residues.

5. The immunoassay method according to claim 1, wherein in formula (1), $R^2$ and $R^3$ are chlorine, $R^1$ and $R^4$ are hydrogen, n is 5, and Z represents 1 to 4 amino acid residues.

6. An immunoassay method for determining the concentration of dioxins in a sample, the method comprising the following steps:
   1) allowing target dioxins in the sample and
   a labeled competitive antigen
   to competitively react with a primary anti-dioxin antibody capable of binding to the target dioxins, and
   determining the amount of competitive antigen-antibody complex from a label incorporated into the competitive antigen;

2) allowing the competitive antigen and
a compound of formula (1) of known concentration (1)

wherein $R^1$, $R^2$, $R^3$ and $R^4$ may be the same or different and each represents chlorine or hydrogen, n is an integer from 1 to 10, and Z represents 1 to 100 amino acid residues to competitively react with the primary anti-dioxin antibody, and determining the amount of competitive antigen-antibody complex from a label incorporated into the competitive antigen;

3) preparing a calibration curve using the amount of competitive antigen-antibody complex determined in step 2); and 4) comparing the amount of competitive antigen-antibody complex determined in step 1) with the calibration curve prepared in step 3).

7. The immunoassay method according to claim 6, wherein the competitive antigen is a compound of formula (1) wherein Z is a carrier protein.

8. The immunoassay method according to claim 6, wherein the label is an enzyme, a radioactive substance or a fluorescent substance.

9. The immunoassay method according to claim 6, wherein in formula (1), $R^2$ and $R^4$ are chlorine, $R^1$ and $R^3$ are hydrogen, n is 5, and Z represents 1 to 3 amino acid residues.

10. The immunoassay method according to claim 6, wherein in formula (1), $R^2$ and $R^3$ are chlorine, $R^1$ and $R^4$ are hydrogen, n is 5, and Z represents 1 to 4 amino acid residues.

11. A method of evaluating the toxic equivalent (TEQ) of dioxins in a sample, the method comprising the following steps:

1) allowing target dioxins in the sample and
a competitive antigen
to competitively react with a primary anti-dioxin antibody capable of binding to the target dioxins, and
determining the amount of competitive antigen-antibody complex from a label incorporated into a secondary antibody binding to the primary antibody;

2) allowing the competitive antigen and
a compound of formula (1) of known concentration (1)

wherein $R^1$, $R^2$, $R^3$ and $R^4$ may be the same or different and each represents chlorine or hydrogen, n is an integer from 1 to 10, and Z represents 1 to 100 amino acid residues to competitively react with the primary anti-dioxin antibody, and determining the amount of competitive antigen-antibody complex from a label incorporated into a secondary antibody binding to the primary antibody;

3) preparing a calibration curve using the amount of competitive antigen-antibody complex determined in step 2);

4) comparing the amount of competitive antigen-antibody complex determined in step 1) with the calibration curve prepared in step 3); and 5) calculating the TEQ of dioxins in a sample.

12. The method according to claim 11, wherein the competitive antigen is a compound of formula (1) wherein Z is a carrier protein.

13. The method according to claim 11, wherein the label is an enzyme, a radioactive substance or a fluorescent substance.

14. The method according to claim 11, wherein in formula (1), $R^2$ and $R^4$ are chlorine, $R^1$ and $R^3$ are hydrogen, n is 5, and Z represents 1 to 3 amino acid residues.

15. The method according to claim 11, wherein in formula (1), $R^2$ and $R^3$ are chlorine, $R^1$ and $R^4$ are hydrogen, n is 5, and Z represents 1 to 4 amino acid residues.

16. A method of evaluating the toxic equivalent (TEQ) of dioxins in a sample, the method comprising the following steps:

1) allowing target dioxins in the sample and
a labeled competitive antigen
to competitively react with a primary anti-dioxin antibody capable of binding to the target dioxins, and
determining the amount of competitive antigen-antibody complex from a label incorporated into the competitive antigen;

2) allowing the competitive antigen and
a compound of formula (1) of known concentration (1)

wherein $R^1$, $R^2$, $R^3$ and $R^4$ may be the same or different and each represents chlorine or hydrogen, n is an integer from 1 to 10, and Z represents 1 to 100 amino acid residues to competitively react with the primary anti-dioxin antibody, and determining the amount of competitive antigen-antibody complex from a label incorporated into the competitive antigen;

3) preparing a calibration curve using the amount of competitive antigen-antibody complex determined in step 2);

4) comparing the amount of competitive antigen-antibody complex determined in step 1) with the calibration curve prepared in step 3); and 5) calculating the TEQ of dioxins in a sample.

17. The method according to claim 16, wherein the competitive antigen is a compound of formula (1) wherein Z is a carrier protein.

18. The method according to claim 16, wherein the label is an enzyme, a radioactive substance or a fluorescent substance.

19. The method according to claim 16, wherein in formula (1), $R^2$ and $R^4$ are chlorine, $R^1$ and $R^3$ are hydrogen, n is 5, and Z represents 1 to 3 amino acid residues.

20. The method according to claim 16, wherein in formula (1), $R^2$ and $R^3$ are chlorine, $R^1$ and $R^4$ are hydrogen, n is 5, and Z represents 1 to 4 amino acid residues.

21. The method according to claim 1, wherein in formula (1), $R^2$ and $R^4$ are chlorine, $R^1$ and $R^3$ are hydrogen, n is 5, and Z represents glycylglycine.

22. The method according to claim 1, wherein in formula (1) used in step 2), $R^2$ and $R^4$ are chlorine, $R^1$ and $R^3$ are hydrogen, n is 5, and Z represents glycylglycine and the competitive antigen is a compound of formula (1) wherein $R^1$, $R^2$, $R^3$, and $R^4$ are, independently, a chlorine or hydrogen atom, n is an integer from 1 to 10, and Z is a carrier protein.

23. The method according to claim 6, wherein in formula (1), $R^2$ and $R^4$ are chlorine, $R^1$ and $R^3$ are hydrogen, n is 5, and Z represents glycylglycine.

24. The method according to claim 6, wherein in formula (1) used in step 2), $R^2$ and $R^4$ are chlorine, $R^1$ and $R^3$ are hydrogen, n is 5, and Z represents glycylglycine and the competitive antigen is a compound of formula (1) wherein $R^1$, $R^2$, $R^3$, and $R^4$ are, independently, a chlorine or hydrogen atom, n is an integer from 1 to 10, and Z is a carrier protein.

25. The method according to claim 11, wherein in formula (1), $R^2$ and $R^4$ are chlorine, $R^1$ and $R^3$ are hydrogen, n is 5, and Z represents glycylglycine.

26. The method according to claim 11, wherein in formula (1) used in step 2), $R^2$ and $R^4$ are chlorine, $R^1$ and $R^3$ are hydrogen, n is 5, and Z represents glycylglycine and the competitive antigen is a compound of formula (1) wherein $R^1$, $R^2$, $R^3$, and $R^4$ are, independently, a chlorine or hydrogen atom, n is an integer from 1 to 10, and Z is a carrier protein.

27. The method according to claim 16, wherein in formula (1), $R^2$ and $R^4$ are chlorine, $R^1$ and $R^3$ are hydrogen, n is 5, and Z represents glycylglycine.

28. The method according to claim 16, wherein in formula (1) used in step 2), $R^2$ and $R^4$ are chlorine, $R^1$ and $R^3$ are hydrogen, n is 5, and Z represents glycylglycine and the competitive antigen is a compound of formula (1) wherein $R^1$, $R^2$, $R^3$, and $R^4$ are, independently, a chlorine or hydrogen atom, n is an integer from 1 to 10, and Z is a carrier protein.

* * * * *